(12) United States Patent
Mickel et al.

(10) Patent No.: US 7,767,831 B2
(45) Date of Patent: Aug. 3, 2010

(54) PROCESS FOR PREPARING RENIN INHIBITORS

(75) Inventors: Stuart J Mickel, Lausen (CH); Gottfried Sedelmeier, Schallstadt (DE); Hans Hirt, Reinach (CH); Frank Schäfer, Rheinfelden-Adelhausen (DE); Michael Foulkes, Riehen (CH); Walter Prikoszovich, Schönenbuch (CH)

(73) Assignee: Novartis AG, Basel (CH)

(*) Notice: Subject to any disclaimer, the term of this patent is extended or adjusted under 35 U.S.C. 154(b) by 164 days.

(21) Appl. No.: 11/916,875

(22) PCT Filed: Jun. 6, 2006

(86) PCT No.: PCT/EP2006/005370

§ 371 (c)(1), (2), (4) Date: Dec. 7, 2007

(87) PCT Pub. No.: WO2006/131304

PCT Pub. Date: Dec. 14, 2006

(65) Prior Publication Data

US 2008/0207921 A1 Aug. 28, 2008

(30) Foreign Application Priority Data

Jun. 8, 2005 (GB) .................. 0511686.8

(51) Int. Cl.
*C07D 207/08* (2006.01)
(52) U.S. Cl. .................... 548/570
(58) Field of Classification Search ............... 514/428; 548/570
See application file for complete search history.

(56) References Cited

U.S. PATENT DOCUMENTS

| | | | |
|---|---|---|---|
| 5,559,111 A | 9/1996 | Göschke et al. | 514/227.5 |
| 5,606,078 A | 2/1997 | Göschke et al. | 549/321 |
| 5,627,182 A | 5/1997 | Göschke et al. | 514/237 |
| 5,646,143 A | 7/1997 | Göschke et al. | 514/233.8 |
| 5,654,445 A | 8/1997 | Göschke et al. | 549/321 |
| 5,659,065 A | 8/1997 | Göschke | 560/29 |
| 5,705,658 A | 1/1998 | Göschke et al. | 549/321 |

FOREIGN PATENT DOCUMENTS

EP 0678503 10/1995
WO 2006024501 3/2006

OTHER PUBLICATIONS

"Formal Total Synthesis of the Potent Renin Inhibitor Aliskiren: Application of a SmI2-Promoted Acyl-like Radical Coupling" Lindsay et al., (2006); J. Org. Chem. 71, 4766-4777.
"A Convergent Synthesis of the Renin Inhibitor SPP-100 Using a Nitrone Intermediate" (2001); Dondoni et al., Tetrahedron Letters 42 4819-4823.
"Practical Synthesis of an Orally Active Renin Inhibitor Aliskiren" (2005); Dong et al., Tetrahedron Letters 46 6337-6340.

*Primary Examiner*—Rebecca L Anderson
*Assistant Examiner*—Shawquia Young
(74) *Attorney, Agent, or Firm*—Ann R. Pokalsky, Esq.; Dilworth & Barrese, LLP

(57) ABSTRACT

The present invention provides a novel process, novel process steps and novel intermediates useful in the synthesis of pharmaceutically active compounds, especially renin inhibitors, such as Aliskiren. Inter alia, the invention provides a process for the manufacture of a compound of the formula III,

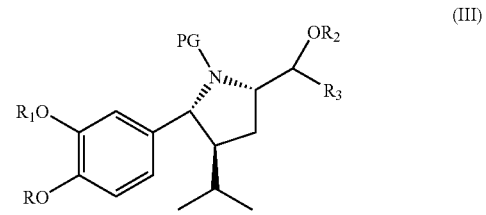

(III)

wherein R, $R_1$, $R_2$, $R_3$ and PG are as defined in the specification, or a salt thereof. The manufacture comprises (preferably consists of) reacting a compound of the formula I,

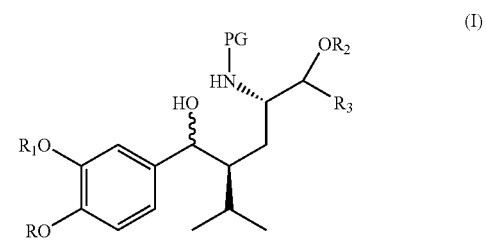

(I)

with a reagent able to transform hydroxy into X where X is for example a leaving group.

2 Claims, No Drawings

PROCESS FOR PREPARING RENIN INHIBITORS

FIELD OF THE INVENTION

The invention relates to a novel process, novel process steps and novel intermediates useful in the synthesis of pharmaceutically active compounds, especially renin inhibitors.

BACKGROUND OF THE INVENTION

Renin passes from the kidneys into the blood where it affects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

With compounds such as (with INN name) aliskiren ((2S,4S,5S,7S)-5-amino-N-(2-carbamoyl-2-methylpropyl)-4-hydroxy-2-isopropyl-7-[4-methoxy-3-(3-methoxypropoxy)benzyl]-8-methylnonanamide), a new antihypertensive has been developed which interferes with the renin-angiotensin system at the beginning of angiotensin II biosynthesis.

As the compound comprises 4 chiral carbon atoms, the synthesis of the enantiomerically pure compound is quite demanding. Therefore, amended routes of synthesis that allow for more convenient synthesis of this sophisticated type of molecules are welcome.

It is therefore a problem to be solved by the present invention to provide new synthesis routes and new intermediates allowing a convenient and efficient access to this class of compounds.

SUMMARY OF THE INVENTION

During investigation into the reductive de-oxygenation of a diastereomeric mixture of secondary benzylic alcohols of the formula I given below, an attempt was made to convert this group into a group other than hydroxy, especially a leaving group such as halo, e.g. chloro or iodo, or a sulfonate of organic sulfonic acids, e.g. methane sulfonate (mesylate) or toluolsulfonate (tosylate), in order to facilitate the reductive process. However, the desired compounds were not obtained. Instead of the desired compounds of the formula II

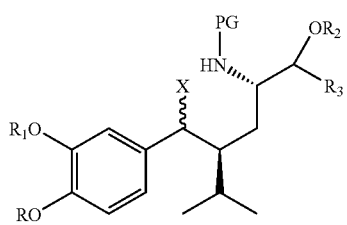

(which then, according to the original intentions, could have been reduced to a corresponding compound wherein instead of X a hydrogen atom is present) wherein R, $R_1$, $R_2$, $R_3$ and PG are as defined for a compound of the formula I below and X is a group other than hydroxy, especially a leaving group such as halo, e.g. chloro or iodo, or a sulfonate of organic sulfonic acids, e.g. methane sulfonate (mesylate) or toluolsulfonate (tosylate), pyrrolidines of the formula III given below are obtained in high yield as single enantiomers, with the stereochemistry as indicated below. This surprising finding was then utilised in a totally new route for the synthesis for aliskiren and related compounds.

DETAILED DESCRIPTION OF THE INVENTION

In a first and very relevant aspect, the invention relates to a process for the manufacture of a compound of the formula III,

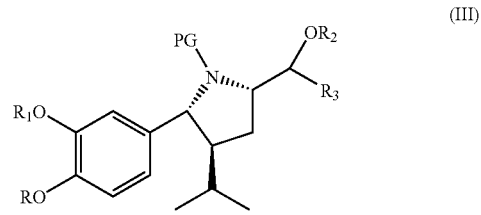

wherein
R is hydrogen, alkyl or alkoxyalkyl;
$R_1$ is hydrogen, alkyl or alkoxyalkyl;
$R_2$ is hydrogen or preferably a hydroxyl protecting group;
$R_3$ is hydrogen or unsubstituted or substituted alkyl; and
PG is an amino protecting group, especially one removable by hydrolysis, e.g. lower alkoxycarbonyl, such as tert-butoxycarbonyl or benzyloxycarbonyl;
or a salt thereof;
said manufacture comprising (preferably consisting in) reacting a compound of the formula I,

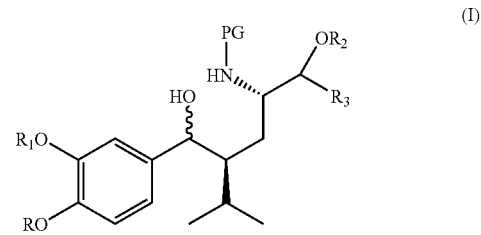

wherein R, $R_1$, $R_2$, $R_3$ and PG are as defined for a compound of the formula III, with a reagent able to transform (here especially benzylic) hydroxy (especially the one bound by a waved bond in formula I) into X (which is presumably at least temporarily present in a transitory compound of the formula II as mentioned above in the reaction mixture before ring formation takes place) where X is a group other than hydroxy or hydrogen, especially a leaving group.

These compounds of formula (I) that are used as starting materials. These are accessible using a synthesis starting from (S) pyroglutamic acid. Reference is made to PCT application WO2006/024501 where ketone amino derivatives of such compounds are prepared that can be converted into the respective amino alcohol by hydrogenation or reduction.

A reagent able to transform hydroxy into X preferably is a customary reagent for the conversion of a benzylic alcohol into a group other than hydroxy, especially leaving group X, e.g. where X is halo selected from the group consisting of (e.g. aqueous) hydrohalic acids, such as hydrochloric acid, a thionyl halogenide, such as thionyl chloride, PX*$_3$, POX*$_3$, PX*$_5$ or POX*$_5$ wherein X* is halogen (so that the X resulting in a, especially chloro or bromo, a combination of triphenylphosphine/halogen, such as triphenylphosphine/iodine, where X is an organic sulfonyloxy moiety an active derivative (formable under comparable conditions as shown below for activation of an active derivative of a carbonic acid of the formula XVI, also in situ, especially an anhydride (e.g. the mixed anhydride with a carbonic acid, such as acetic

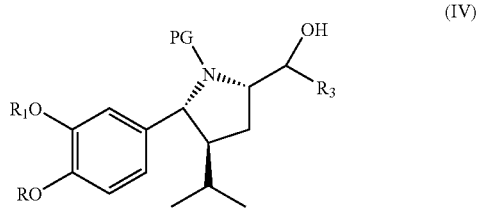

(IV)

wherein R, R$_1$, R$_3$ and PG are as defined under formula III above, or a salt thereof. A compound of the formula IV, or a salt thereof, is also as such a preferred embodiment of the invention.

In the case of a protecting group R$_2$ removable by hydrolysis, e.g. tert-C$_4$-C$_7$-alkoxycarbonyl such as tert-butoxycarbonyl, the removal preferably takes place in the presence of an acid or more preferably a base, such as a metal hydroxide or preferably a metal, more preferably an alkalimetal carbonate, such as potassium carbonate, in an appropriate solvent, such as an alcohol, e.g. methanol or ethanol, water or a mixture thereof, e.g. at temperatures from 0° C. to the reflux temperature of the mixture, for example from 30 to 60° C.

As an alternative to reaction steps described above, compound (I)— also crude (I)—can be transformed in a one-pot synthesis to compound (IV) as the free base (IVa), which may be purified by extraction, without isolation of the intermediate compound of formula (III). compound (IVa) then can be crystallized as a salt such as the maleate or oxalate. This is preferred as it allows further purification. Compound (IVa) is easily transformed to compound (IV). The introduction of the protecting group at the nitrogen is simple, selective and clean.

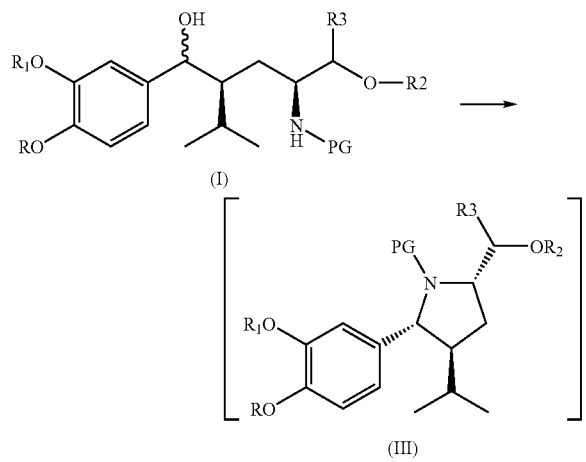

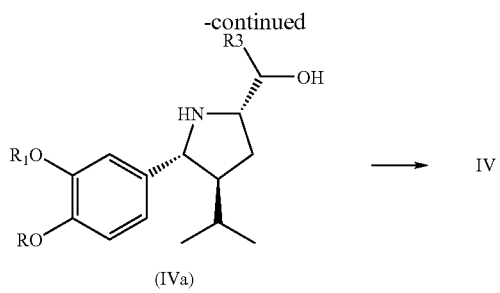

(IVa)

In this sequence, a protecting group R$_2$ and PG are preferably removable by hydrolysis and are more preferably, e.g. tert-C$_4$-C$_7$-alkoxycarbonyl such as tert-butoxycarbonyl. The removal preferably takes place in the presence of an base or more preferably an acid under conditions well known in the art, such as using an inorganic acid preferably as an aqueous or alcoholic solution thereof such as HCl, trifluoroacetic acid, sulfuric acid, phosphoric acid, methane sulfonic acid, etc. in an appropriate solvent, such as an alcohol, e.g. methanol or ethanol, esters like ethylacetate or isopropyl acetate, or ethers like THF or TBME, water or a mixture thereof, e.g. at temperatures from 0° C. to the reflux temperature of the mixture, for example from 50 to 100° C.

If a crystallization of compound (IVa) is desired, this is performed by typical crystallization techniques and adding the desired acid such as maleic acid or oxalic acid, preferably maleic acid.

Protection of the pyrrolidine amino group is effected by methods known in the art such as those described hereinafter in the examples or as referred to in the cited textbooks. Preferably, a boc group is introduced at the nitrogen using e.g. di-tert-butyl dicarbonate under standard conditions.

A compound of the formula IV can then be further used in a number of ways in the synthesis of renin inhibitors such as aliskiren. acid, or a symmetric anhydride) or halogenide of an organic sulfonic acid, such as methanesulphonyl chloride, trifluoromethanesulfonylchloride or tosylchloride, in the presence of a base, e.g. a tertiary nitrogen base, such as triethylamine, or the like. In the case of a thionyl halogenide, PX*$_3$, POX*$_3$, PX*$_5$ or POX*$_5$, the reaction preferably takes place in an appropriate solvent, such as toluene, in the presence of a tertiary nitrogen base, such as pyridine, e.g. at reaction temperatures from 0 to 50° C. In the presence of an anhydride or halide of an organic sulfonic acid, the reaction preferably takes place in the presence of an appropriate solvent, such as toluene and/or dimethylaminopyridine, and a base, e.g. a tertiary nitrogen base, such as triethylamine, e.g. at temperatures from −30 to 50° C. In the presence of triphenylphosphine/halogen, the reaction preferably takes place in an appropriate solvent, such as toluene and/or acetonitrile, in the presence of a (preferably cyclic unsaturated) nitrogen base, such as imidazole, at temperatures e.g. from 0 to 50° C.

Alternatively, compound (III) can be obtained from compound (I) using an ion exchange resin, preferably an acidic ion exchange resin such an amberlyst acidic ion exchange resin, preferably Amberlyst 15 (Fluka) under the elimination of water. The reaction preferably takes place in the presence of an appropriate solvent, such as toluene and/or acetonitrile, at temperatures e.g. from 0 to 50° C. such as room temperature.

Another important embodiment of the invention relates to a compound of the formula III as defined above, or a salt thereof.

A compound of the formula III may be used, inter alia, for the synthesis of pharmaceutically active substances, preferably renin inhibitors such as aliskiren, especially as described in the following.

In a preferred further embodiment of the invention, this synthesis comprises as a further step or as individual synthesis the (partial) deprotection of a compound of the formula III (which in free form or as salt is also as such a preferred embodiment of the invention) wherein $R_2$ is a hydroxy protecting group, especially one removable by deprotection conditions other than those required for removal of PG, more preferably by hydrolysis, e.g. tert-$C_4$-$C_7$-alkoxacarbonyl, such as tert-butoxycarbonyl, while R, $R_1$, $R_3$ and PG are as defined for a compound of the formula I above, under removal of the protecting group $R_2$ to a compound of the formula IV.

In a first further embodiment of the invention, a process for the synthesis of a renin inhibitor, such as aliskiren, comprises oxidizing a compound of the formula IV, especially synthesized as in the preceding steps, to an oxo compound of the formula V,

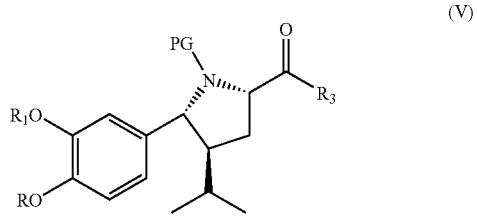

(V)

wherein R, $R_1$, $R_3$ and PG are as defined under formula III above, or a salt thereof. This process step as such, as well as a compound of the formula V, or a salt thereof, also form embodiments of the invention.

The reaction especially takes place under customary conditions that allow for the oxidation of a hydroxy group to an oxo group and employing customary oxidizing reagents (oxidants).

In the (preferred) case where $R_3$ in a compound of a formula IV is hydrogen, this reaction can make use of such oxidants that allow for the direct obtaining from a compound of the formula IV of a corresponding aldehyde of the formula V, or a salt thereof, or it can be lead by first oxidizing to a carboxyl compound of the formula XVI,

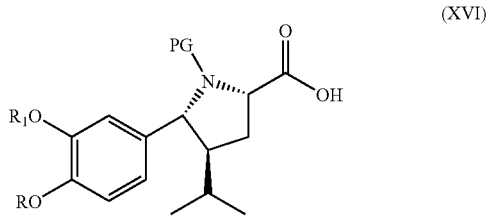

(XVI)

wherein R, $R_1$ and PG are as defined above for a compound of the formula III, or a salt thereof, which can then be reduced with reducing agents to an aldehyde of the formula V wherein $R_3$ is hydrogen and wherein R, $R_1$, $R_3$ and PG are as defined under formula III above, or a salt thereof. These process steps as such, as well as a compound of the formula XVI, or a salt thereof, and a compound of the formula V, or a salt thereof, also form embodiments of the invention. The direct reaction to an aldehyde of the formula V, can, for example, take place in the presence of an oxidant that allows for the oxidation of an alcohol to an aldehyde without undue formation of the acid of the formula XVI, e.g. under Oppenauer conditions (e.g. using cyclohexanone, cinnamic aldehyde or anisaldehyde as oxidant in the presence of an aluminium alcoholate, such as aluminium-tert.-butoxyalcoholate), preferably with chromic acid, dichromate/sulphuric acid, pyridinium-chlorochromate, pyridinium dichromate, nitric acid, manganese dioxide or selenium dioxide or by catalytic dehydrogenation, or more preferably using oxidants useful under mild reaction conditions, such as TEMPO oxidation (TEMPO=2,2,6,6-tetramethylpiperidine-nitroxyl) with bleach, e.g. sodium sodium chlorite or calcium hypochlorite, preferably in the presence of a bromide salt, e.g. potassium bromide, in an appropriate solvent, such as methylene chloride and/or water, or with diacetoxyiodobenzene in an appropriate solvent, e.g. methylene chloride, at temperatures e.g. from 0 to 50° C.; under Swern conditions, e.g. using dimethylsulfoxide in the presence of oxalyl chloride, e.g. at lowered temperatures, such as from −90 to 0° C., preferably in the presence of a tertiary nitrogen base, such as triethylamine or diisopropylethylamine; under Corey-Kim conditions, e.g. using dimethylsulfide in the presence of N-chloro-succinimide; using Moffat-Pfitzner conditions, e.g. oxidation with dimethylsulfoxide in the presence of dicyclohexylcarbodiimide; Dess-Martin oxidation in the presence of Dess-Martin-periodinane (1,1,1-triacetoxy-1,1-dihydro-1,2-benziodoxol-3(1H)-one) in an appropriate solvent, such as methylene chloride, e.g. at temperatures from 0 to 50° C.; or using $SO_3$/pyridine complex in dimethylsulfoxide in the absence or presence of an appropriate solvent such as methylene chloride at temperatures e.g. from −30 to 30° C.; or with lower preference using catalytic dehydrogenation, e.g. in the presence of silver, copper, copper chromium oxide or zinc oxide. Where required, the stoichiometry of the oxidants is chosen appropriately to avoid over-oxidation.

The oxidation of a compound of the formula IV (or also an aldehyde compound of the formula V obtained preferably as described above) to a compound of the formula XVI can, for example, take place with Jones reagent ($CrO_3$ in aqueous sulphuric acid/acetone), with manganese dioxide, with pyridinium dichromate or especially under Pinnick oxidation conditions, e.g. by oxidation with sodium chlorite or calcium hypochlorite in the presence of a weak acid, preferably an alkalimetal dihydrogenphosphate, e.g. sodium dihydrogenphosphate, in an appropriate solvent or solvent mixture, e.g. an alcohol, such as tert-butanol, 2-methyl-2-butene and/or water, at temperatures e.g. from 0 to 50° C. The reduction of an acid compound of the formula XVI then can take place using reducing agents that allow for the selective reduction to an aldehyde of the formula V wherein $R_3$ is hydrogen and wherein R, $R_1$, $R_3$ and PG are as defined under formula II. The reducing agents can, for example, be selected from appropriate complex hydrides, such as, and the compound of the formula XVI can also be used in a form with activated carboxyl group, e.g. as acid halogenide, active ester, (e.g. mixed) anhydride or by in situ activation, e.g. in an active form or by activation as described below for the coupling of a compound of the formula XVI and a compound of the formula VI. For example, in the case of an acid chloride of a compound of the formula XVI, the reduction to an aldehyde of the formula V can take place with LiAlH(tert-butoxy)$_3$ (lithium-tri(tert-butoxy)aluminiumhydride) in an appropriate solvent, e.g. 2-methoxyethyl ether (diglyme), or sodium borohydride or complexes thereof can be used. Alternatively, the reduction can take place by hydrogenation in the presence of partially poisoned hydrogenation catalysts, e.g. under Rosenmund reduction conditions using palladium/barium sulfate and hydrogen in an appropriate solvent, such as water, an alcohol, such as methanol or ethanol, dioxane, acetyl acetate or mixture of two or more such solvents, at customary temperatures, e.g. from 0 to 80° C.

In a further embodiment of said first embodiment of the invention, a process for the synthesis of a renin inhibitor, such as aliskiren, comprises reacting a compound of the formula V as just defined with the proviso that $R_3$ in it is hydrogen under Grignard or Grignard-like conditions with a reagent prepared by reaction of a compound of the formula VI,

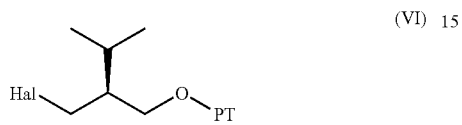

wherein Hal is halo, preferably chloro, bromo or iodo, and PT is a hydroxyl protecting group, with a metal, to give a compound of the formula VII,

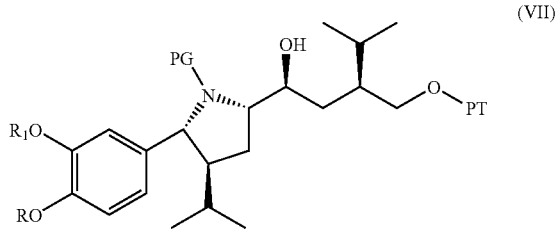

wherein R, $R_1$ and PG are as defined under formula III and PT is a hydroxyl protecting group, preferably one that can be selectively removed without removal of the protecting group PG, e.g. 1-phenyl-$C_1$-$C_7$-alkyl, such as benzyl, or a salt thereof. This process step as such, as well as a compound of the formula VII, or a salt thereof, also form embodiments of the invention. The diastereoselectivity of this reaction can be very high, e.g. larger than 99:1, that is, the other possible diastereoisomer is practically not observed. This shows a high advantage of the use of the pyrrolidine ring system for this conversion and thus also in the synthesis of renin inhibitors such as aliskiren.

The reaction preferably takes place with a metal reacting with the compound of the formula VI to give the corresponding metal compound, e.g. a lithium, sodium, iron, zinc, tin, indium, manganese, aluminium or copper metal compound, or MnX, (alkyl)$_3$MnLi—, or —CeX$_2$ wherein X is halogen such as Cl, I or Br, more preferably Br; or further a reagent obtainable with metal combinations, such as Mg/Fe, or still further with Lewis acids, such as BF$_3$.diethyl ether complex or MgBr$_2$, or the like, to give a Grignard-like reagent for Grignard-like reaction, or with magnesium giving the corresponding Grignard reagent with magnesium (Mg) as the metal for Grignard reaction, in an appropriate solvent, e.g. an ether, such as a cyclic ether, e.g. tetrahydrofuran, an alkyl ether, e.g. diethyl ether, tert-butylmethyl ether, a hydrocarbon, such as toluene, or a halogenated hydrocarbon, e.g. methylene chloride, at temperatures e.g. in the range from 0 to 70° C. Grignard or Grignard-like reagents or organo lithium compounds are preferred, and Grignard or Grignard-like reagents are particularly preferred.

Compound of formula (VI) can be prepared according to methods well known to the person skilled in the art, see e.g., Houben-Weyl, Vol. 13/2a, page 53-526, which is incorporated herein by reference.

In a further embodiment of said first embodiment of the invention, a process for the synthesis of a renin inhibitor, such as aliskiren, comprises deprotecting a compound of the formula VII as just defined by removal of the hydroxy protecting group PT, for example in the case of a protecting group that can be removed by hydrogenation such as 1-phenyl-$C_1$-$C_7$-alkyl, e.g. benzyl, by catalytic hydrogenation, to give a compound of the formula VIII,

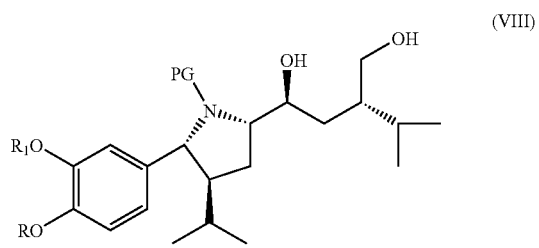

wherein R, $R_1$ and PG are as defined under formula III above, or a salt thereof. This process step as such, as well as a compound of the formula VIII, or a salt thereof, also form embodiments of the invention. The deprotection takes place under standard conditions, e.g. in the case of removal of the protecting group by hydrogenation with hydrogen in the presence of a catalyst, such as a noble metal catalyst, e.g. palladium, which may be present on a carrier, such as charcoal, in an appropriate solvent, such as an alcohol, e.g. methanol or ethanol, or non-alcoholic solvents such as (but not restricted to) toluene or ethyl acetate, at appropriate temperatures, e.g. in the range from 0 to 50° C.

In a further embodiment of said first embodiment of the invention, a process for the synthesis of a renin inhibitor, such as aliskiren, comprises oxidizing a compound of the formula VIII at the primary hydroxy group to an aldehyde compound of the formula IX,

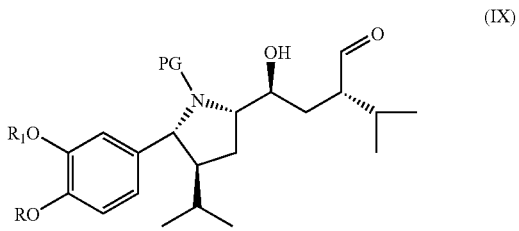

wherein R, $R_1$ and PG are as defined under formula III above, or a salt thereof, which then cyclizes spontaneously to produce a lactol of the formula X,

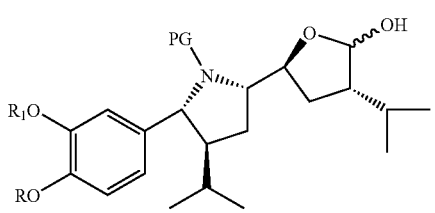

which, either in the same reaction mixture (in situ) or after isolation and in a separate process step, which as such also forms an embodiment of the invention, is then oxidized to a lactone of the formula XI,

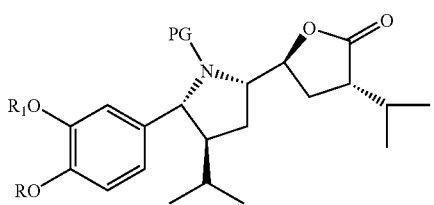

wherein in formula X and XI R, $R_1$ and PG are as defined for a compound of the formula III above. This sequence of reaction steps from reaction of a compound of the formula VIII to a compound of the formula XI as such, as well as a compound of the formula IX or especially a compound of the formula X and/or XI, or salts thereof, also form embodiments of the invention. The oxidation of a compound of the formula VIII resulting in the lactol of the formula X preferably takes place under the conditions mentioned to be preferred for oxidation of a compound of the formula IV to an aldehyde of the formula V, e.g. with $SO_3$/pyridine in the presence of dimethylsulphoxide in an appropriate solvent, such as methylene chloride, preferably in the presence of a tertiary nitrogen base, such as triethylamine, e.g. at temperatures from −30 to 50° C. The subsequent oxidation to the compound of the formula XI can take place under the same reaction conditions employing an excess of some of the reagents mentioned above or it can be isolated and oxidized separately with further reagents, e.g. those mentioned above, more preferably using TEMPO/diacetoxyiodo benzene.

Alternatively, it can also be oxidized at the primary alcohol without effecting the secondary alcohol to compound XI with the reagent TPAP (Tetra-N-propylammonium perruthenate) e.g. according to lit. ref., S. Ley et al. Synthesis, 639 (1994). This method is particularly preferred.

In a further embodiment of said first embodiment of the invention, a process for the synthesis of a renin inhibitor, such as aliskiren, comprises reacting a compound of the formula XI as just defined, or a salt thereof, with an amine of the formula XII,

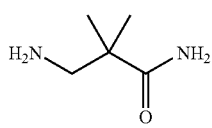

(wherein the amido nitrogen can also be protected if desired and the protecting group then be removed in the corresponding protected compound of the formula XIII), or a salt thereof, obtaining a compound of the formula XIII,

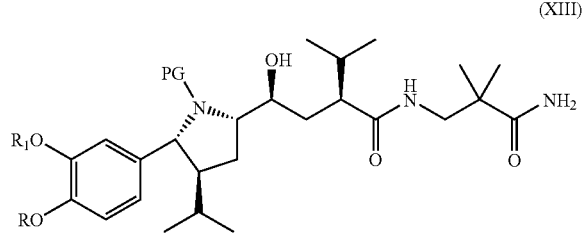

wherein R, $R_1$ and PG are as defined for a compound of the formula III, or a salt thereof. This process step as such, as well as a compound of the formula XIII, or a salt thereof, also form embodiments of the invention.

The reaction preferably takes place under standard conditions for the formation of an amide from a lactone, e.g. in an appropriate solvent or solvent mixture, e.g. in an ether, such as tert-butylmethyl ether, preferably in the presence of a bifunctional catalyst with a weak acidic and a weak basic group, e.g. 2-hydroxypyridine or proline, in the presence of an appropriate base, e.g. a tertiary nitrogen base, such as triethylamine, at appropriate temperatures e.g. in the range from 0° C. to the reflux temperature of the reaction mixture, e.g. from 0 to 85° C.

In a further embodiment of said first embodiment of the invention, a process for the synthesis of a renin inhibitor, such as aliskiren, comprises opening the ring in a compound of the formula XIII by reductive or hydrogenolytic ring opening to a compound of the formula XIV,

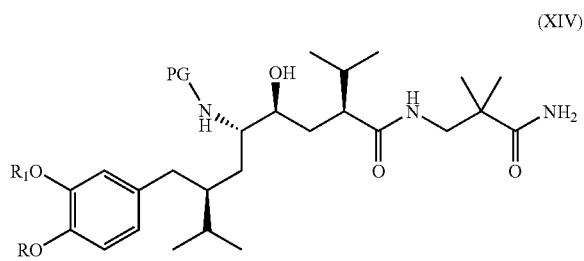

wherein R, $R_1$ and PG are as defined for a compound of the formula III, or a salt thereof. This reaction step as such also forms an embodiment of the invention.

The reductive ring opening preferably takes place under conditions employing appropriate metals as reductants, e.g. under conditions comparable to those of a Birch reduction with alkali metals and liquid ammonia, e.g. with sodium or lithium in the presence of liquid ammonia ($NH_3$) in the presence or absence of an appropriate further solvent or solvent mixture, such as an ether, e.g. tetrahydrofurane, and/or an alcohol, e.g. ethanol, at lower temperatures, e.g. from −90 to −20° C., e.g. at about −78° C. Alternative reductions methods are possible, e.g. reduction with calcium in tert-butanol, other reduction methods with calcium, lithium-di-tert-butylbiphenylide, magnesium in anthracene, or the like, which do not require the use of liquid ammonia and low temperatures (<−20° C.).

Alternatively, the ring opening may be effected by hydrogenation. Such methods are well known in the art and are described e.g. in Houben-Weyl, Volume 11/1, Stickstoffverbindungen II, page 968-971 or D. Tourwé, et al., Tetrahedron, 54, 1753 (1998).

In a further embodiment of said first embodiment of the invention, a process for the synthesis of a renin inhibitor, such as aliskiren, comprises deprotecting a compound of the formula XIV to give the corresponding compound of the formula XV,

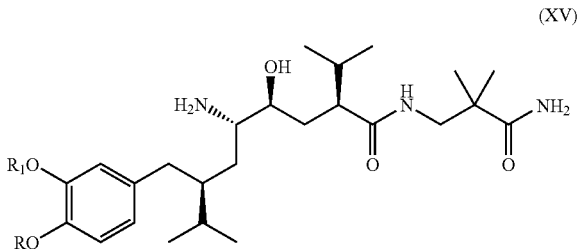

(XV)

which is pharmaceutically active, especially as a renin inhibitor, wherein R and $R_1$ are as defined for a compound of the formula I, or a salt thereof; and, if desired, converting an obtainable free compound of the formula XV into a salt or an obtainable salt into the free compound of the formula XV or a different salt thereof. For example, if PG is (what is preferred) a $C_1$-$C_7$-alkoxycarbonyl group, such as tert-butoxycarbonyl, the removal can take place under customary conditions, e.g. in the presence of an acid, such as hydrohalic acid, in an appropriate solvent, such as dioxane, e.g. at temperatures from 0 to 50° C., for example at room temperature.

An especially important aspect of the invention relates to a process for the manufacture of a compound of the formula XV, or a salt thereof, comprising first opening the ring in a compound of the formula XIII as described above by reducing it selectively to a compound of the formula XIV as described above, or a salt thereof, and then deprotecting a compound of the formula XIV to give the corresponding compound of the formula XV, or a salt thereof, and, if desired, converting an obtainable free compound of the formula XV into a salt or an obtainable salt into the free compound of the formula XV or a different salt thereof.

In a second further embodiment according to the invention, a process for the synthesis of a renin inhibitor, such as aliskiren, comprises reacting a compound of the formula XVI (which can be obtained as described above or by first oxidizing a compound of the formula IV wherein $R_3$ is hydrogen, this reaction can make use of such oxidants that lead to a corresponding aldehyde of the formula V, or a salt thereof, and then oxidizing the aldehyde of the formula V further to the carbonic acid of the formula XVI, or a salt thereof, e.g. by reactions analogous to those described above) as described above, or a salt thereof (obtainable preferably as described above where the synthesis of a compound of the formula XVI is first described) wherein R, $R_1$ and PG are as defined above for a compound of the formula III, or a salt thereof, with a reagent capable of activating the carboxyl group, especially capable of transforming it into an acid halide, a mixed acid anhydride, a carbonyl imidazolide or a "Weinreb amide", and then reacting it with a metallo-organic derivative of a compound of the formula VI as defined above, especially a zinc, lithium or magnesium derivative, to a compound of the formula XVII,

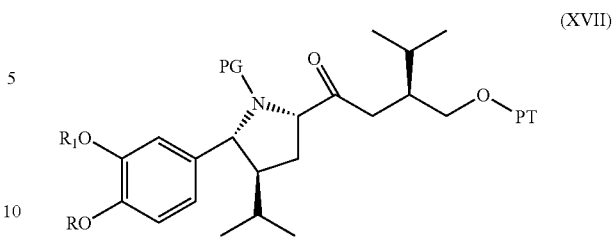

(XVII)

wherein R, $R_1$ and PG are as defined for a compound of the formula III and PT is as defined for a compound of the formula VI, or a salt thereof. This process step as such, as well as a compound of the formula XVII, or a salt thereof, also form embodiments of the invention.

The activating of the carboxyl group in a compound of the formula XVI to form a reactive derivative thereof preferably takes place under customary condensation conditions, where among the possible reactive derivatives of an acid of the formula XVI reactive esters (such as the hydroxybenzotriazole (HOBT), pentafluorophenyl, 4-nitrophenyl or N-hydroxysuccinimide ester), imidazolide, a "Weinreb amide", acid halogenides (such as the acid chloride or bromide) or reactive anhydrides (such as mixed anhydrides with lower alkanoic acids or symmetric anhydrides) are preferred. Reactive carbonic acid derivatives can also be formed in situ. The reaction is carried out by dissolving the compounds of formula XVI in a suitable solvent, for example a halogenated hydrocarbon, such as methylene chloride, N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and, if the reactive derivative of the acid of the formula II is formed in situ, a suitable coupling agent that forms a preferred reactive derivative of the carbonic acid of formula XVI in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)N,N,N', N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. The reaction mixture is preferably stirred at a temperature of between approximately −20 and 50° C., especially between 0° C. and 30° C., e.g. at room temperature. The reaction is preferably carried out under an inert gas, e.g. nitrogen or argon.

The subsequent reaction with a metallo-organic derivative of a compound of the formula VI, especially a zinc, lithium or magnesium derivative, or further a manganese, aluminium or copper derivative, then preferably takes place under customary conditions, e.g. analogous to the Grignard or Grignard-like conditions mentioned above for the reaction of a compound of the formula VI with an aldehyde of the formula V.

In a further embodiment of said second embodiment of the invention, a process for the synthesis of a renin inhibitor, such as aliskiren, comprises reducing a compound of the formula XVII under stereoselective conditions and deprotecting the resulting compound under removal of the hydroxy protecting group PT to give a compound of the formula VIII as described above, or a salt thereof.

The reduction under stereoselective conditions preferably takes place in the presence of a stereoselective reductant, such as LiAlH(O-tert-butyl)$_3$, LiBH(sec-butyl)$_3$ (Selectride®), potassium selectride, or borohydride/oxaazaborolidine (("CBS-catalysts" originally based on the work of Corey, Bakshi and Shibata, synthesizable in situ from an amino alcohol and borane), or by stereoselective hydrogenation, e.g. in the presence of catalysts such as [Ru$_2$Cl$_4$((S- or R-)BI-NAP)]NEt$_3$; the reactions take place under customary conditions, e.g. in appropriate solvents, such as tetrahydrofuran, methanol, ethanol, or mixtures of two or more such solvents, e.g. at temperatures from −80 to 50° C. (see, for example, Rüeger et al., Tetrahedron Letters, 2000, 41, 10085.)

The deprotection then takes place under standard conditions, e.g. if PT is a protecting group that can be removed by hydrogenation such as 1-phenyl-C$_1$-C$_7$-alkyl, e.g. benzyl, by catalytic hydrogenation, for example under conditions analogous to those mentioned above for deprotection of a compound of the formula VII.

A compound of the formula VIII can be further reacted to a compound of the formula X, or a salt thereof, as described above, which then can be further reacted via the reaction steps shown above to yield a compound of the formula XV, or a salt thereof.

Alternatively, a compound of the formula VIII as defined above, or a salt thereof, obtainable or preferably obtained either according to the first or the second embodiment of the invention, can be further reacted to a compound of the formula XVIII,

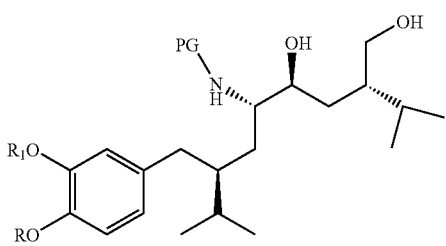

(XVIII)

wherein R, R$_1$ and PG are as defined for a compound of the formula III, or a salt thereof, by reductive or hydrogenolytic ring opening of the pyrrolidine ring. This process step as such, as well as a compound of the formula XVIII, or a salt thereof, also form an embodiment of the invention. The reductive or hydrogenolytic ring opening preferably takes place under conditions as those mentioned above for the ring opening in a compound of the formula XIV.

Alternatively, a compound of the formula VII as defined above, or a salt thereof, obtainable or preferably obtained either according to the first or the second embodiment of the invention, can be further reacted to a compound of the formula XVIII directly without a separate deprotection step,

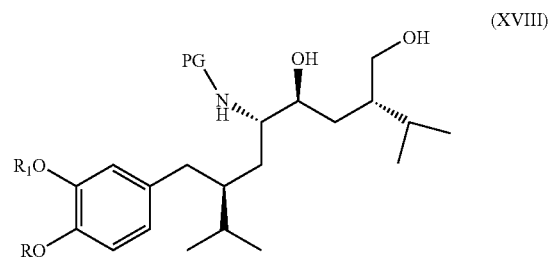

(XVIII)

wherein R, R$_1$ and PG are as defined for a compound of the formula III, or a salt thereof, by reductive or hydrogenolytic ring opening of the pyrrolidine ring. This process step as such, as well as a compound of the formula XVIII, or a salt thereof, also form an embodiment of the invention. The reductive or hydrogenolytic ring opening preferably takes place under conditions as those mentioned above for the ring opening in a compound of the formula XIV. This method is particularly preferred when PT is a protecting group removable under the conditions of the reductive opening, in particular, if PT is phenyl-C$_1$-C$_7$-alkyl, such as benzyl.

A compound of the formula XVIII can then be oxidized in a further embodiment of said first or second embodiment of the invention in a process for the synthesis of a renin inhibitor, such as aliskiren, (comparably as a compound of the formula VIII via an aldehyde with opened pyrrolidine ring analogous to a compound of the formula IX, preferably under conditions as described for that reaction) to a lactol of the formula XIX,

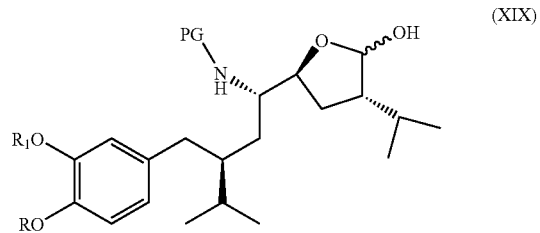

(XIX)

wherein R, R$_1$ and PG are as defined for a compound of the formula III, or a salt thereof (where both this reaction as well as a compound of the formula XIX, or a salt thereof, as such are also embodiments of the present invention), which, either in the same reaction mixture (in situ) or after isolation, is then oxidized to a lactone of the formula XX

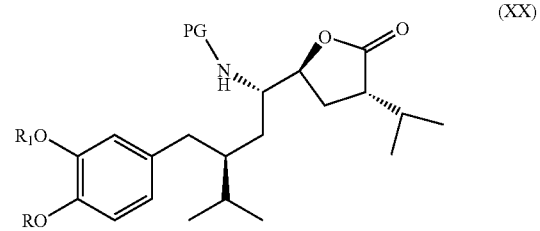

(XX)

wherein R, R$_1$ and PG are as defined for a compound of the formula III, or a salt thereof (where this reaction as such is also an embodiment of the present invention), the reaction preferably taking place under conditions analogous to those described above for oxidation a compound of the formula X to a compound of the formula XI. A lactone of the formula XX, or a salt thereof, can also be obtained directly from a compound of the formula XVIII. In this case, the reaction also preferably taking place under conditions analogous to those described above for oxidation a compound of the formula X to a compound of the formula XI A lactone of the formula XX, or a salt thereof, is also a preferred new embodiment according to the invention.

A compound of the formula XX can then, in a further embodiment of said first or second embodiment of the invention in a process for the synthesis of a renin inhibitor, such as aliskiren, be reacted with a compound of the formula XII defined above (if in protected form with subsequent deprotection of the amide nitrogen), preferably under analogous reaction conditions as described there, to a compound of the formula XIV as described above, or a salt thereof (where this reaction as such also is an embodiment of the invention. The latter can then be deprotected as described above to give the final product of the formula XV described above, or a salt thereof.

In a third embodiment of the invention, a process for the synthesis of a renin inhibitor, such as aliskiren, comprises reacting a compound of the formula VII, or a salt thereof, as defined above (obtainable according to the first or second embodiment of the invention) by reductive or hydrogenolytic ring opening to a compound of the formula XXI,

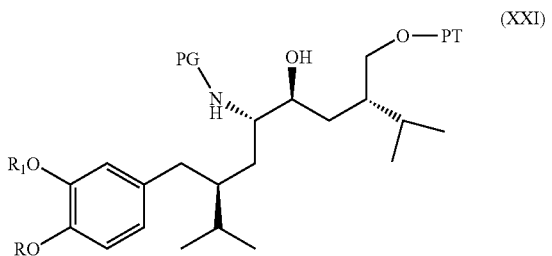

wherein R, $R_1$ and PG are as defined for a compound of the formula III and PT is a hydroxy protecting group, or a salt thereof, (where this reaction step as such, as well as a compound of the formula XXI, or a salt thereof, especially wherein PG=benzyloxycarbonyl and PT is benzyl or wherein PG is hydrogen and PT is benzyl, also form embodiments of the invention. The reductive or hydrogenolytic ring opening preferably takes place under conditions as those mentioned above for the ring opening in a compound of the formula XIV. A compound of the formula XXI, or a salt thereof, can then be reacted in analogy to a compound of the formula VIII above by removal of the protecting group to give a compound of the formula XVIII as described above, or a salt thereof, which can then be further transformed e.g. via compounds XIX and XX and XIV and preferably under analogous reaction conditions, or in each case a salt thereof, to a compound of the formula XV as defined above, or a salt thereof.

In a fourth embodiment of the invention, a process for the synthesis of a renin inhibitor, such as aliskiren, comprises reacting a compound of the formula X, or a salt thereof, as defined above, by reductive or hydrogenolytic ring opening to a compound of the formula XIX as shown above, or a salt thereof, which reaction as such is also an embodiment of the invention. The reductive or hydrogenolytic ring opening preferably takes place under conditions as those mentioned above for the ring opening in a compound of the formula XIV.

In a further embodiment of said fourth embodiment of the invention, a process for the synthesis of a renin inhibitor, such as aliskiren, comprises oxidising a compound of the formula XIX, or a salt thereof, to give a lactone compound of the formula XX, or a salt thereof, as described above (preferably under reaction conditions analogous to those for oxidation of a compound of the formula X to a compound of the formula XI as given above) which, in yet a further embodiment of said fourth embodiment of the invention, can then be reacted with a compound of the formula XII, or a salt thereof, as described above, preferably under reaction conditions analogous to those described for reaction of a compound of the formula XI with a compound of the formula XII, to give a compound of the formula XIV as described above, or a salt thereof, which can then, in a further embodiment of said fourth embodiment of the invention, be deprotected into a compound of the formula XV, or a salt thereof, as described above, preferably under analogous conditions as described above for the deprotection of a compound of the formula XIV.

In a fifth embodiment of the invention, a process for the synthesis of a renin inhibitor, such as aliskiren, comprises reacting a compound of the formula XI as described above, or a salt thereof, by reductive or hydrogenolytic ring opening to give a compound of the formula XX, or a salt thereof, as described above (where this reaction as such also forms an embodiment of the invention). The reductive or hydrogenolytic ring opening preferably takes place under conditions as those mentioned above for the ring opening in a compound of the formula XIV.

In a further embodiment of said fifth embodiment of the invention, a process for the synthesis of a renin inhibitor, such as aliskiren, comprises reacting a compound of the formula XX, or a salt thereof, with a compound of the formula XII, or a salt thereof, as described above, preferably under reaction conditions analogous to those mentioned above for reaction of a compound of the formula XI with a compound of the formula XII, to give a compound of the formula XIV as described above, or a salt thereof, which can then, in a further embodiment of said fifth embodiment of the invention, be deprotected into a compound of the formula XV, or a salt thereof, as described above, preferably under reaction conditions analogous to those described above for deprotection of a compound of the formula XIV.

In a sixth embodiment of the invention, a process for the synthesis of a renin inhibitor, such as aliskiren, comprises reacting a compound of the formula V as described above, or a salt thereof, wherein $R_3$ is hydrogen, with a compound of the formula XXII,

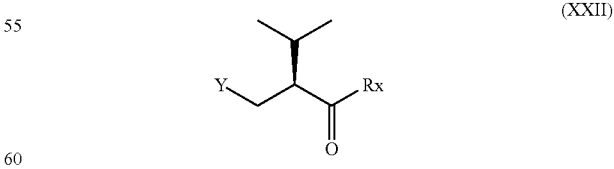

wherein Y is $Ph_3P^+$ or $(AlkO)_2P(O)$ wherein Alk is preferably alkyl, e.g. $C_1$-$C_7$-alkyl, (both of which may also be prepared in situ, respectively) and Rx is hydroxy, protected hydroxy, amino or $NH-CH_2C(CH_3)_2-CONH_2$, resulting in a compound of the formula XXIII,

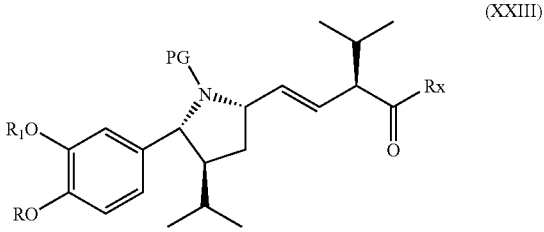

(XXIII)

wherein R, $R_1$ and PG are as defined for a compound of the formula III and Rx is as defined for a compound of the formula XXII; or a salt thereof. This process step as such, as well as a compound of the formula XXIII, or a salt thereof, also form embodiments of the invention. Here the reaction can take place in the presence of a suitable base, for example, sodium hydride, butyllithium, hexyllithium, cyclohexyllithium or lithium diisopropylamide, in appropriate solvents, such as ethers, e.g. tetrahydrofuran, hydrocarbons, e.g. toluene, or halogenated hydrocarbons, e.g. methylene chloride or mixtures of two or more such solvents, for example at temperatures between −78° C. and 100° C.

In a further embodiment of said sixth embodiment of the invention, a process for the synthesis of a renin inhibitor, such as aliskiren, comprises reacting a compound of the formula XXIII, or a salt thereof, under reductive or hydrogenolytic opening of the pyrrolidine ring and formation of an aziridino ring in formula XXIII to give a compound of the formula XXIV,

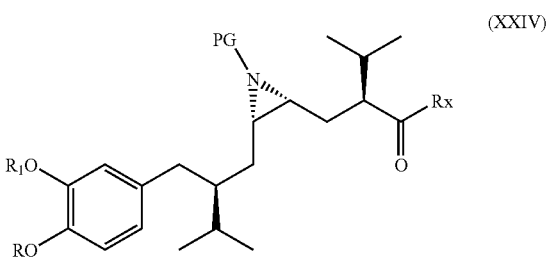

(XXIV)

wherein R, $R_1$ and PG are as defined for a compound of the formula III and Rx is as defined for a compound of the formula XXII, or a salt thereof. This process step as such, as well as a compound of the formula XXIV, or a salt thereof, also form embodiments of the invention. The reductive or hydrogenolytic ring opening preferably takes place under conditions as those mentioned above for the ring opening in a compound of the formula XIV.

In a further embodiment of said sixth embodiment of the invention, a process for the synthesis of a renin inhibitor, such as aliskiren, comprises reacting a compound of the formula XXIV, or a salt thereof, under ring opening to give a compound of the formula XX, or a salt thereof, if Rx in the compound of the formula is OH (or if it is protected hydroxy and the hydroxy protecting group is first removed to give OH). The ring opening reaction can, for example, take place under acidic or basic conditions, preferably in the presence of appropriate solvents, for example alcohols, such as ethanol or methanol, ethers, such as tetrahydrofuran, hydrocarbons, such as toluene, or halogenated hydrocarbons, such as methylene chloride, for example at temperatures between 0° C. and the reflux temperature of the respective reaction mixture.

A compound of the formula XX, or a salt thereof, can then, in a further preferred embodiment of the sixth embodiment of the invention, be converted into a compound of the formula XIV as described above, or a salt thereof, by reacting it with a compound of the formula XII as defined above to a compound of the formula XIV as defined above, preferably under reaction conditions analogous to those mentioned above; which, in a further preferred embodiment of the sixth embodiment of the invention, can then be deprotected to a compound of the formula XV, or a salt thereof, preferably under conditions analogous to those described above for deprotection of a compound of the formula XIV.

In yet a further embodiment of said sixth embodiment of the invention, a process for the synthesis of a renin inhibitor, such as aliskiren, comprises reacting a compound of the formula XXIV, or a salt thereof, wherein Rx is NH—$CH_2C(CH_3)_2$—$CONH_2$, under ring opening (with conditions preferably analogous to those described in the preceding paragraph) to give a compound of the formula XIV, or a salt thereof. The latter can then, in a further preferred embodiment of this version of the sixth embodiment of the invention, be deprotected to a compound of the formula XV, or a salt thereof, preferably under conditions analogous to those described above for deprotection of a compound of the formula XIV.

All these different synthesis routes show that with the compound of the formula III a highly important new compound has been found that is a central intermediate to a number of possible synthesis routes especially for the synthesis of renin inhibitors such as aliskiren. Therefore, this compound of the formula III, or a salt thereof, as well as its synthesis form very highly preferred embodiments of the invention.

Listed below are definitions of various terms used to describe the novel intermediates and synthesis steps of the present invention. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

The term "lower" or "$C_1$-$C_7$—" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

Halo or halogen is preferably fluoro, chloro, bromo or iodo, most preferably fluoro, chloro or bromo; where halo is mentioned, this can mean that one or more (e.g. up to three) halogen atoms are present, e.g. in halo-$C_1$-$C_7$-alkyl, such as trifluoromethyl, 2,2-difluoroethyl or 2,2,2-trifluoroethyl.

Alkyl preferably has up to 20 carbon atom and is more preferably $C_1$-$C_7$-alkyl. Alkyl is straight-chained or branched (one or, if desired and possible, more times). Very preferred is methyl.

Alkoxyalkyl is alkyl (which is preferably as just defined) that is substituted at a carbon, preferably at a terminal carbon (in ω-position), with an alkyloxy (=alkoxy) group wherein alkyl is as defined above, preferably $C_1$-$C_7$-alkoxy. As alkoxyalkyl, 3-methoxypropyl is especially preferred.

Protecting groups may be present (see also under "General Process Conditions") and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. Preferably, if two or more protecting groups are present in one intermediate mentioned herein, they are chosen so that, if one of the groups needs to be removed, this can be done selectively, e.g. using two or more different protecting groups that are cleavable under different conditions, e.g. one class by mild hydrolysis, the other by hydrolysis under harder conditions, one class by hydrolysis in the presence of an acid, the other by hydrolysis in the presence of a base, or one class by reductive cleavage (e.g. by catalytic hydrogenation), the other by hydrolysis, or the like.

As hydroxyl protecting group, any group that is appropriate for reversible protection of hydroxy groups is possible, e.g. those mentioned in the standard textbooks under "General Process Conditions". A hydroxyl protecting group may, just to mention a few examples, be selected from a group comprising (especially consisting of) a silyl protecting group, especially diaryl-lower alkyl-silyl, such as diphenyl-tert-butylsilyl, or more preferably tri-lower alkylsilyl, such as tert-butyldimethylsilyl or trimethylsilyl; an acyl group, e.g. lower alkanoyl, such as acetyl; benzoyl; lower alkoxycarbonyl, such as tert-butoxycarbonyl (Boc), or phenyl-lower alkoxycarbonyl, such as benzyloxycarbonyl; tetrahydropyranyl; unsubstituted or substituted 1-phenyl-lower alkyl, such as benzyl or p-methoxybenzyl, and methoxymethyl. Boc (selectively removable by hydrolysis) and benzyl (selectively removable by hydrogenation) are especially preferred.

As amino protecting group, any group that is appropriate for reversible protection of hydroxy groups is possible, e.g. those mentioned in the standard textbooks under "General Process Conditions". An amino protecting group may, just to mention a few examples, be selected from a group comprising (especially consisting of) acyl (especially the residue of an organic carbonic acid bound via its carbonyl group or an organic sulfonic acid bound via its sulfonyl group), arylmethyl, etherified mercapto, 2-acyl-lower alk-1-enyl, silyl or N-lower alkylpyrrolidinylidene. Preferred amino-protecting groups are lower alkoxycarbonyl, especially tert-butoxycarbonyl (Boc), phenyl-lower alkoxycarbonyl, such as benzyloxycarbonyl, fluorenyl-lower alkoxycarbonyl, such as fluorenylmethoxycarbonyl, 2-lower alkanoyl-lower alk-1-en-2-yl and lower alkoxycarbonyl-lower alk-1-en-2-yl, with most preference being given to iso-butyryl, benzoyl, phenoxyacetyl, 4-tert-butylphenoxyacetyl, N,N-dimethylformamidinyl, N-methylpyrrolidin-2-ylidene or especially tert-butoxycarbonyl.

A group X other than hydroxy or hydrogen is preferably a leaving group, e.g. halo, such as chloro, bromo or iodo, or the acyloxy moiety derived from an organic sulfonic acid, such as a alkanesulfonyloxy, especially $C_1$-$C_7$-alkanesulfonyloxy, e.g. methanesulfonyloxy, haloalkanesulfonyloxy, especially halo-C1-$C_7$-alkanesulfonyloxy, such as trifluoromethanesulfonyloxy, or unsubstituted or substituted arylsulfonyloxy, such as toluolsulfonyloxy (tosyloxy).

Unsubstituted or substituted aryl is preferably a mono- or polycyclic, especially monocyclic, bicyclic or tricyclic aryl moiety with 6 to 22 carbon atoms, especially phenyl (very preferred), naphthyl (very preferred), indenyl, fluorenyl, acenapthylenyl, phenylenyl or phenanthryl, and is unsubstituted or substituted by one or more, especially one to three, moieties, preferably independently selected from the group consisting of $C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycarbonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfo, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro.

Salts are especially the pharmaceutically acceptable salts of compounds of formula XV or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds of formula XV or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethanesulfonic acid, ethane-1,2-disulfonic acid, benzenesulfonic acid, 2-naphthalenesulfonic acid, 1,5-naphthalenedisulfonic acid, N-cyclohexylsulfamic acid, N-methyl-, N-ethyl- or N-propylsulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula XV or any of the intermediates mentioned herein may also form internal salts.

For isolation or purification purposes of compounds of the formula XV or in general for any of the intermediates mentioned herein it is also possible to use pharmaceutically unacceptable salts, for example picrates or perchlorates. For therapeutic use, only pharmaceutically acceptable salts or free compounds of the formula XV are employed (where applicable comprised in pharmaceutical preparations), and these are therefore preferred at least in the case of compounds of the formula XV.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula XV, is to be understood as referring also to one or more salts thereof or a mixture of a corresponding free compound, intermediate or starting material and one or more salts thereof, each of which is intended to include also any solvate, metabolic precursor such as ester or amide of the compound of formula XV, or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

Starting materials are especially the compounds of the formula I, VI, XII and/or XXI mentioned herein, intermediates are especially compounds of the formula III, IV, V, VII, VIII, IX, X, XI, XIII, XIV, XVI, XVII, XVIII, XIX, XX, XXI, XXIII and/or XXIV.

The invention relates also to methods of synthesis of the starting materials (e.g. of the formula I, VI, XII and/or XXI) and especially the intermediates of the formula III, IV, V, VII, VIII, IX, X, XI, XIII, XIV, XVI, XVII, XVIII, XIX, XX, XXI, XXIII and XXIV mentioned above from their respective precursors as mentioned above, including methods with the single steps of a sequence leading to a compound of the formula XV, more than one or all steps of said synthesis and/or pharmaceutically active substances, especially renin inhibitors, most preferably aliskiren, including methods with the single steps of a sequence leading to a compound of the formula XV, more than one or all steps of said synthesis and/or pharmaceutically active substances, and/or their use in the synthesis of pharmaceutically active compounds, such as renin inhibitors, especially aliskiren.

General Process Conditions

The following, in accordance with the knowledge of a person skilled in the art about possible limitations in the case of single reactions, applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula XV is designated a "protecting group", unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/1, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage). Different protecting groups can be selected so that they can be removed selectively at different steps while other protecting groups remain intact. The corresponding alternatives can be selected readily by the person skilled in the art from those given in the standard reference works mentioned above or the description or the Examples given herein.

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about $-100°$ C. to about $190°$ C., preferably from approximately $-80°$ C. to approximately $150°$ C., for example at from $-80$ to $-60°$ C., at room temperature, at from $-20$ to $40°$ C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning. Where required or desired, water-free or absolute solvents can be used.

Where required, the working-up of reaction mixtures, especially in order to isolate desired compounds or intermediates, follows customary procedures and steps, e.g. selected from the group comprising but not limited to extraction, neutralization, crystallization, chromatography, evaporation, drying, filtration, centrifugation and the like.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula XV—scribed as being preferred. Special preference is given to reaction conditions that are identical or analogous to those mentioned in the Examples. The invention relates also to novel starting compounds and intermediates described herein, especially those leading to compounds mentioned as preferred herein.

The invention especially relates to any of the methods described hereinbefore and hereinafter that leads to aliskiren, or a pharmaceutically acceptable salt thereof.

The following Examples serve to illustrate the invention without limiting the scope thereof, while they on the other hand represent preferred embodiments of the reaction steps, intermediates and/or the process of manufacture of aliskiren, or salts thereof.

Where mentioned in the Examples, "boc" stands for tert-butoxycarbonyl.

EXAMPLES

I. Synthesis of (1S,3S,5S)-5-tert-Butoxycarbonyloxymethyl-3-isopropyl-2-[4-methoxy-3-(3-methoxy-propoxy)-phenyl]pyrrolidine-1-carboxylic acid tert-butyl ester 3

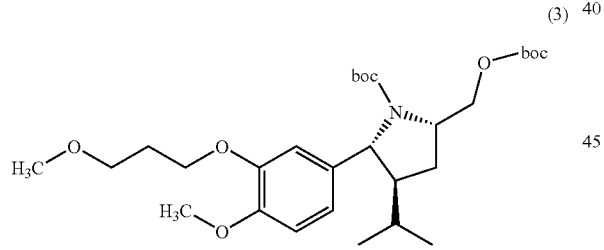

(3)

A Variant employing thionyl chloride: A solution of 2.16 g of carbonic acid (2S,4S)-2-tertbutoxycarbonylamino-4-[4-methoxy-3-(4-methoxy-butyl)-benzyl]5-methyl-hexyl ester tert-butyl ester 1 in 30 mL of dry toluene is treated with 1.07 g of pyridine and 0.68 g of thionyl chloride is added dropwise at room temperature. The mixture is stirred at room temperature for 3 hours and 0.22 g of ethanol and 30 mL of water are added. The two phase system is extracted and the organic layer removed and washed with 20 mL of 10% aqueous sodium hydrogen sulphate solution followed by 20 mL of saturated aqueous sodium bicarbonate solution. Finally the organic phase is washed twice with 20 mL of water and the solvent removed in vacuum to give an oil. Chromatography on silica-gel, eluting with heptane/ethyl acetate mixtures provides e.g. 1.04 g of 3 as an oil with a negative $[a]_d$ (measured: e.g. −39.1) at c=1, CHCl$_3$.

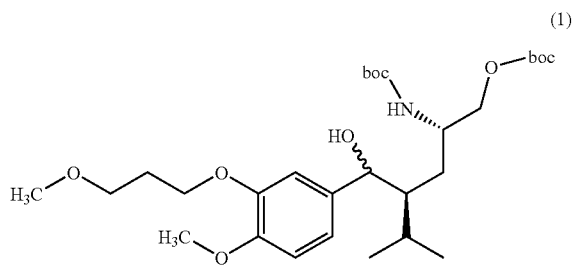

(1)

B Variant employing methanesulphonyl chloride: A solution of 1.98 g of carbonic acid (2S,4S)-2-tertbutoxycarbonylamino-4-[4-methoxy-3-(4-methoxy-butyl)-benzyl]5-methylhexyl ester tert butyl ester 1 in 20 mL of dry toluene is treated with 0.044 g of dimethylaminopyridine and 0.55 g of triethylamine and cooled to 0° C. Methanesulphonyl chloride (0.43 g) is added dropwise and the reaction mixture is warmed to room temperature and stirred for 30 hours. The mixture is diluted with 20 mL of water and the organic layer separated. The organic layer is washed with 20 mL of saturated aqueous sodium bicarbonate solution and finally the organic phase is washed twice with 20 mL of water and the solvent removed in vacuum to give an oil. Chromatography on silica-gel, eluting with heptane/ethyl acetate mixtures provides e.g. 1.64 g of 3 as an oil. The product shows a negative $[a]_d$ (measured: e.g. −39.1) at c=1, CHCl$_3$.

C Variant employing triphenylphosphine/iodine: A solution of 1.48 g of carbonic acid (2S,4S)-2-tertbutoxycarbonylamino-4-[4-methoxy-3-(4-methoxy-butyl)-benzyl]5-methylhexyl ester tert butyl ester 1 in 15 mL of dry toluene/acetonitrile (85/15) is treated with 0.58 g of imidazole at room temperature. Triphenylphosphine (1.14 g) is added, followed by dropwise addition of a solution of 1.11 g of iodine in 15 Ml of toluene/acetonitrile (85/15) within 15 minutes. The reaction mixture is stirred at room temperature for 4 hours and quenched with 20 mL of a 5% solution of sodium thiosulphate. The organic phase is separated and washed twice with 20 mL of brine. The solvent is removed under vacuum and the resulting oil is chromatographed on silica-gel to give e.g. 1.24 g of 3 as an oil.

D Variant employing ion exchange resin:

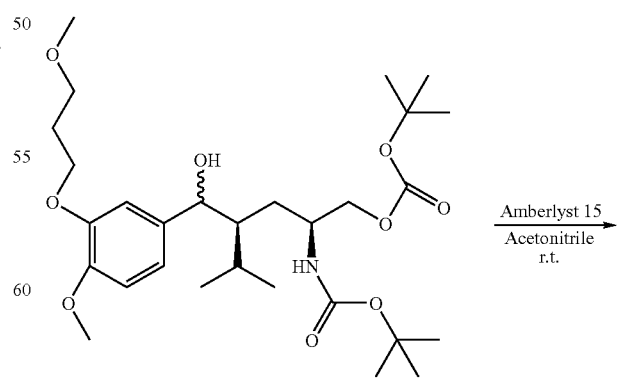

Exact Mass = 555
Molecular Formula = C29H49NO9

-continued

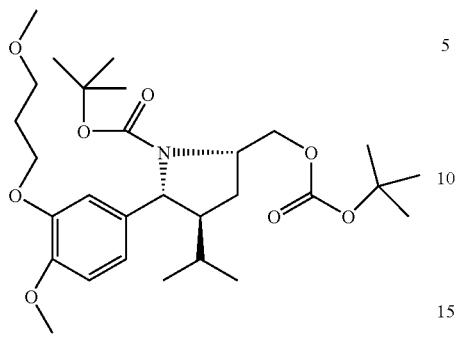

Exact Mass = 537
Molecular Formula = C29H47NO8

45.70 g of carbonic acid (2S,4S)-2-tertbutoxycarbonylamino-4-[4-methoxy-3-(4-methoxybutyl)-benzyl]5-methyl-hexyl ester tert butyl ester 1 (HPLC 95.0% b.a., 78.1 mmol) are at r.t. dissolved in 390 ml of acetonitrile. To the solution are added 11.6 g (55.0 mequ) Amberlyst 15 (Fluka 06423, 4.7 mequ/g). The resulting mixture is stirred at r.t. for 5 hours. Then filtration and evaporation of the filtrate at 50° C. and 20 mbar afford the residue as a clear colourless oil. Purity HPLC 97.2% b.a.

The starting material 1 can be prepared according to the following method:

Preparation of compound 1 by reduction of the corresp. aryl ketone with LiBH$_4$ In a 350 ml three necked flask are dissolved 34.5 g (62.3 mmol) of bis-Boc-aryl ketone in 400 ml of ethanol and 3.5 ml of water. To this solution is added a solution of 40.7 g of LiBH$_4$ in 32 ml of THF via a dropping funnel within 15 min. at room temperature. The dropping funnel is rinsed with 8 ml of THF and the reaction mixture is stirred at room temperature over night. Then an additional amount of 13.6 g of LiBH$_4$ in a mixture of 10 ml THF and 1 ml of water is added. The reaction mixture is warmed to 40° C. for 2 hours and is then cooled to 0° C. The reaction is quenched with 125 ml acetic acid followed by an extractive work up with 500 ml of water and 500 ml of TBME. The organic phase is dried via sodium sulfate and evaporated in vacuum to give a very viscous oil which consist as a mixture of epimeric benzylic alcohols in the ratio (8:1).

II. Synthesis of (2R,3S,5S)-5-Hydroxymethyl-3-isopropyl-2-[4-methoxy-3-(3 methoxypropoxy)-phenyl]pyrrolidine-1-carboxylic acid tert-butyl ester 6

(6)

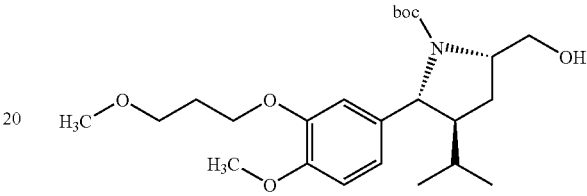

A solution of 2.52 g pyrrolidine 3 in 2.5 mL of methanol is treated with 3.87 g of potassium carbonate, and the suspension is warmed to 45° C. and stirred at this temperature for 4 hours. The reaction is then diluted with 60 mL of tert-butylmethyl ether and 20 mL of water and the mixture extracted. The organic layer is separated and the aqueous layer is washed with a further charge of 40 mL of tert-butylmethyl ether. The combined organic layers are washed twice with 20 mL of water and the solvent is removed in vacuum to give the alcohol 6 as an oil. A negative [a]$_d$ is found at c=1, CHCl$_3$. $^1$H-NMR (d$^6$-DMSO/D$_2$O, 300K) 6.90-6.80 (3H), 4.03-3.90 (3H), 3.80 (1H), 3.75 (3H), 3.55-3.45 (3H), 3.23 (3H), 3.05 (1H), 2.00-1.80 (3H), 1.65 (1H), 1.40 (9H), 1.20 (1H), 0.74 (6H).

Alternative route to (2R,3S,5S)-5-Hydroxymethyl-3-isopropyl-2-[4-methoxy-3-(3 methoxypropoxy)-phenyl]pyrrolidine-1-carboxylic acid tert-butyl ester 6

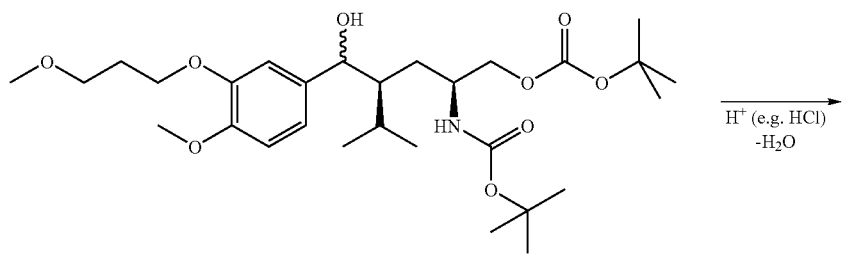

(1) Mixture of epimeres
555.7

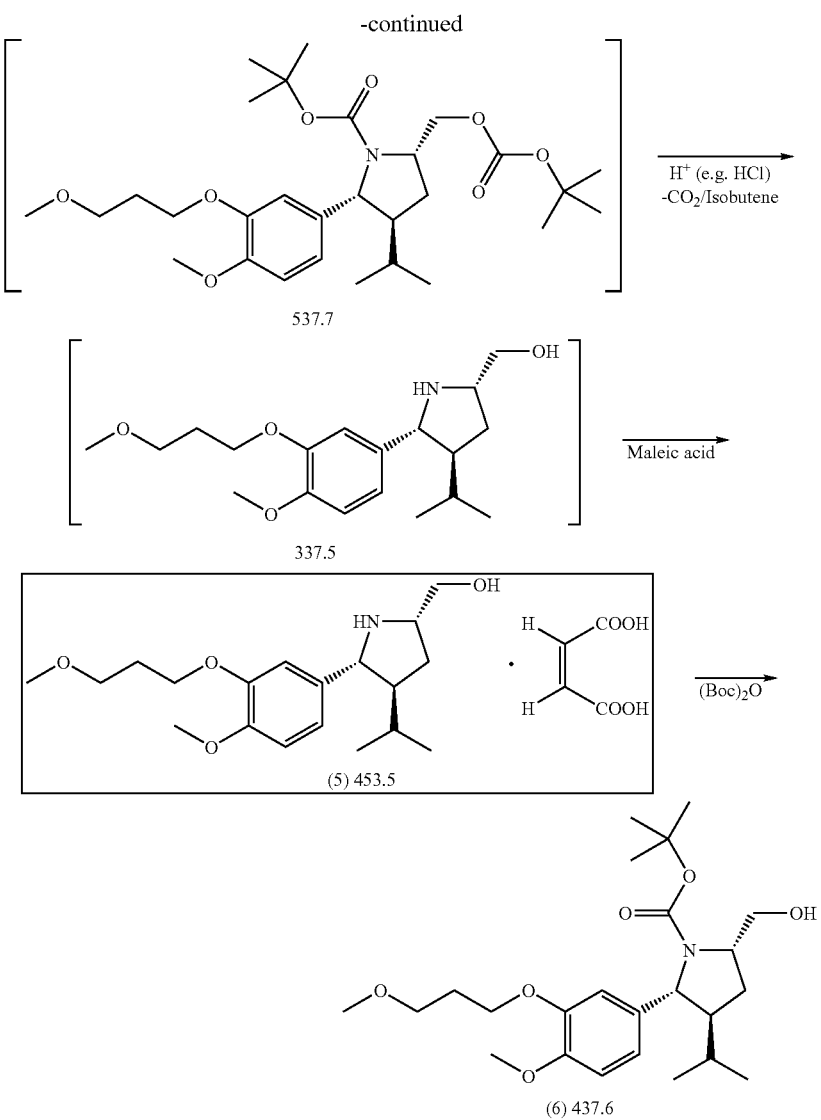

Synthesis of {(2S,4S,5R)-4-Isopropyl-5-[4-methoxy-3-(3-methoxy-propoxy)-phenyl]pyrrolidin-2-yl}-methanol (Z)-but-2-enedioic acid 1/salt 6

To a solution of 5.56 g of carbonic acid (2S,4S)-2-tertbutoxycarbonylamino-4-[4-methoxy-3-(4-methoxy-butyl)-benzyl]5-methyl-hexyl ester tert-butyl ester (1) in 28 ml ethanol absolute, 2.5 ml of aqueous hydrochloric acid 37% (or an equivalent amount of hydrochloride acid in ethanol 2 M) is added at 0-5° C. After stirring for 1 h at 0-5° C., the reaction mixture is gradually heated to 78-80° C. within 1 h. Stirring at reflux temperature is continued for 2-4 h, until transformation is complete. The reaction mixture is cooled to RT, and 18 ml of water is added. The organic solvent (ethanol) is stripped off in vacuo, and the remaining aqueous concentrate is extracted with 12 ml isopropylacetate. The aqueous layer is separated, and after addition of 30 ml isopropylacetate, approximately 3.2 ml aqueous sodium hydroxide solution 30% is slowly added at 0-5° C. under vigorous agitation, until pH 11-12 is reached. The organic layer is separated and concentrated to approximately 25 ml residual volume (azeotropic removal of remaining water).

A solution of 1.16 g maleic acid in 12 ml isopropanol is added to the concentrate of intermediate (5) free base in isopropylacetate at 40° C. Crystallization of (5) maleate is initiated by seeding at 40° C. and completed by cooling of the suspension to 0-5° C. The crystalline (5) maleate 1/1 salt is collected by filtration, washed with 16 ml isopropylacetate/isopropanol 3/1 (v) and dried in vacuo. $^1$H-NMR (d$^6$-DMSO, 300 K): 7.2 (1H), 6.9-7.1 (2H), 6.0 (2H), 5.3 (1H), 4.1-4.2 (1H), 3.9-4.1 (2H), 3.8 (1H), 3.6-3.7 (3H), 3.4-3.5 (2H), 3.3 (3H), 2.4-2.5 (1H), 1.9-2.0 (3H), 1.8-1.9 (1H), 1.6-1.7 (1H), 0.8-0.9 (3H), 0.7-0.8 (3H).

Synthesis of (2R,3S,5S)-5-Hydroxymethyl-3-isopropyl-2-[4-methoxy-3-(3-methoxy-propoxy)phenyl]-pyrrolidine-1-carboxylic acid tert-butyl ester (6)

2.27 g (5) maleate 1/1 salt is dissolved in a mixture of 10 ml methylenechloride and 8 ml water. 8 ml aqueous sodium hydroxide solution 2.0 M is added at 0-5° C. under vigorous stirring. Then a solution of 1.14 g di-tert-butyl-dicarbonate in 10 ml methylene chloride is added within 10 min. After 15 min at 0-5° C., the reaction mixture is slowly heated to room temperature and further agitated for approximately 0.5 h.

The organic phase is separated, washed with water, dried over sodium sulfate or by azeotropic destillation and finally evaporated in vacuo. The remaining crude (6)—or a concentrate of the product in methylenechloride—can be directly further processed to (7) according to patent example below.

III. Synthesis of (2R,3S,5S)-5-Formyl-3-isopropyl-2-[4-methoxy-3-(3 methoxy-propoxy)-phenyl]pyrrolidine-1-carboxylic acid tert-butyl ester 7

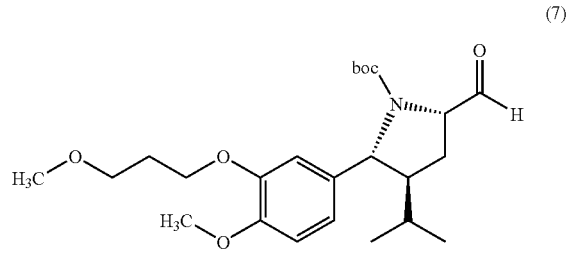

(7)

Using SO$_3$/pyridine complex: A solution of 4.7 g of alcohol 6 in 58 ml of methylene chloride is treated with 33 mL of dimethylsulphoxide and 5.67 g of triethylamine is added. The mixture is cooled to 0° C. and a solution of 6.84 g of the SO$_3$/pyridine complex dissolved in 46 mL of dimethyl sulphoxide is added dropwise within 20 minutes. The reaction is stirred at 0° C. for 2 hours and quenched with 105 mL of water and 105 mL of heptane. The organic layer is separated and washed with 25 mL of 10% aqueous sodium hydrogen sulphate solution. The organic phase is then washed with 110 mL of water followed by 25 mL of saturated aqueous sodium hydrogen carbonate solution. Finally the organic phase is washed with water until the pH of the aqueous solution is 7. The solvent is then removed to give the aldehyde 7 as an oil. A negative $[a]_d$ is found at c=1, CHCl$_3$. $^1$H-NMR (d$^6$-DMSO, 300K) 9.75 (1H), 6.90-6.80 (3H), 4.63-4.30 (3H), 4.00 (2H), 3.75 (3H), 3.50 (3H), 3.23 (3H), 2.10-1.90 (4H), 1.85 (1H), 1.60 (1H), 1.05 (9H), 0.85 (6H).

Alternatively, to a solution of 1.1 g of the alcohol 6 in 10 mL of dichloromethane is added 0.4 g of pyridine, 1.1 g of diisopropylethylamine and 2.0 g of dimethyl sulfoxide. The mixture is cooled to −5° C. and 0.6 g of sulfur trioxide-pyridine complex is added in four portions over a period of 2 h. The reaction is quenched by addition of 2.5 mL of water and acidified by addition of 1 mL of 37% hydrochloric acid. The phases are separated and the organic phase washed with 2.5 mL of water, dried over sodium sulfate and the solvent removed in-vacuum, to afford e.g. 0.88 g of the aldehyde 7 as an oil.

Using TEMPO: A mixture of 0.96 g of the alcohol 6, 0.044 g of sodium hydrogencarbonate, 0.026 g of potassium bromide and 0.051 g of TEMPO in 3 mL of dichloromethane and 1.2 mL of water is cooled to 5° C. To the mixture is added dropwise 0.13 g of 10-13% sodium hypochlorite solution, and the mixture stirred for 5 h between 5° C. and 20° C., before addition of 0.57 g of sodium sulfite. The phases are then separated and the organic phase washed twice with 5 mL of water. Evaporation of the solvent in vacuum affords e.g. 0.50 g of the aldehyde 7 as an oil.

IV. Synthesis of (2R,3S,5S)-4-isopropyl-5-[4-methoxy-3-(3 methoxy-propoxy)-phenyl]pyrrolidine-1,2-dicarboxylic acid 1-tert-butyl ester 15

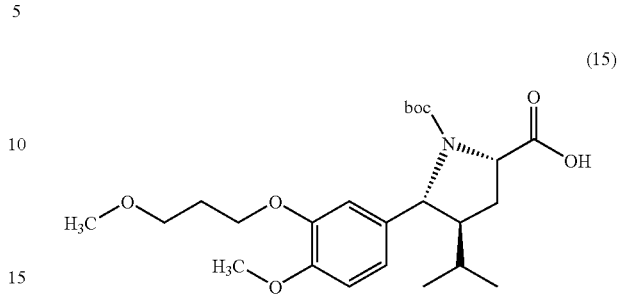

(15)

A solution of 1.7 g of the aldehyde 7 in 15 mL of tert-butanol is treated with 3 mL of 2-methyl-2-butene. A solution of 0.43 g of sodium chlorite and 1.73 g of sodium dihydrogen phosphate in 15 mL of water is added dropwise. The two phase mixture is stirred for 90 minutes at room temperature and 15 mL of toluene and 15 mL of water is added. The organic layer is separated and washed with 20 mL of water. The solvent is removed in vacuum to give the acid 15 as a clear oil which slowly crystallizes. $^1$H-NMR (d$^6$-DMSO, 354K) 12.25 (1H), 7.35 (1H), 6.90 (1H), 6.81 (1H), 4.38 (1H), 4.25 (1H), 4.00 (2H), 3.75 (3H), 3.45 (2H), 3.23 (3H), 2.15-1.85 (4H), 1.65 (1H), 1.25 (9H), 0.85 (6H).

V. Synthesis of (2R,3S,5S)-5-((1S,3S)-3-Benzyloxymethyl-1-hydroxy-4-methyl-pentyl)-3-isopropyl-2-[4-methoxy-3-(3 methoxy-propoxy)-phenyl]pyrrolidine-1-carboxylic acid tert-butyl ester 8

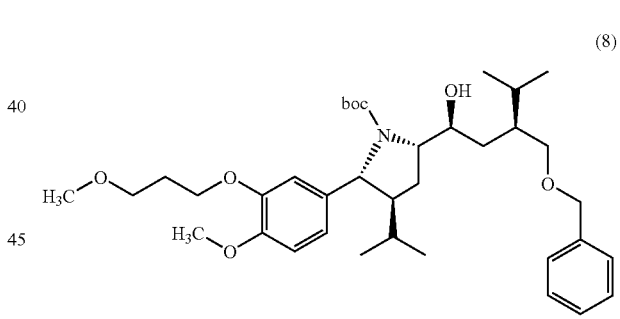

(8)

A solution of 1.98 g of aldehyde 7 in 15 mL of tetrahydrofuran is cooled to 10° C. and is treated with the Grignard reagent prepared by treating 1.23 g of ((S)-2-bromomethyl-3-methylbutoxymethyl)-benzene with 0.12 g of magnesium in diethylether containing 0.043 g of 1,2-dibromoethane at 45° C. The reaction is stirred for 90 minutes at room temperature, then 20 mL of a 25% aqueous solution of ammonium chloride is added, followed by addition of 20 mL of tert-butylmethyl ether. The organic phase is separated and washed twice with 20 mL of water. The organic phase is concentrated in vacuum to give the crude alcohol 8 as an oil. Purification on silica-gel delivers e.g. 0.97 g of pure 8. A negative $[a]_d$ is found at c=1, CHCl$_3$. M$^+$+H=628, M$^+$+H+Na=650.

Alternatively, A solution of 27 g of aldehyde 7 in 30 mL of tetrahydrofuran is added to a room-temperature solution of the Grignard reagent prepared by refluxing 20 g of ((S)-2-chloromethyl-3-methyl-butoxymethyl)-benzene with 3.2 g of magnesium in 120 mL of tetrahydrofuran containing 1.3 g of 1,2-dibromoethane for 4 h. The reaction is stirred for 1 h at room temperature, then 100 mL of 2 N sulfuric add is added. The mixture is stirred until the excess magnesium has dissolved, then the phases are separated and the organic phase washed with 50 mL of 12% sodium chloride solution. The organic phase is concentrated in vacuum to give e.g. 42.6 g of the crude alcohol 8 as an oil.

VI. Synthesis of (2R,3S,5S)-5-((1S,3S)-1-Hydroxymethyl-3-hydroxymethyl-4-methylpentyl)-3-isopropyl-2-[4-methoxy-3-(3 methoxy-propoxy)-phenyl]pyrrolidine-1-carboxylic acid tert-butyl ester 9

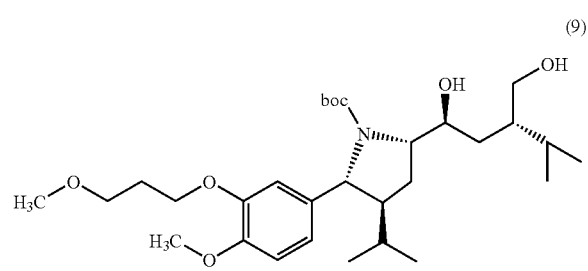

(9)

A solution of 0.48 g of 8 in 1.5 mL of methanol is treated with 0.1 g of 10% palladium on charcoal. The suspension is stirred under an atmosphere of hydrogen until the uptake is stable. The suspension is filtered and the solid washed with 5 mL of methanol in two portions. Removal of the solvent in vacuum provides alcohol 9 as an oil. A negative $[a]_d$ (e.g. −34.1, −34.6) is found at c=1, $CHCl_3$.

VIa. Synthesis of ((1S,2S,4S)-2-Hydroxy-4-hydroxymethyl-1-{(S)-2-[4-methoxy-3-(3-methoxy-propoxy)-benzyl]-3-methyl-butyl}-5-methyl-hexyl)-carbamic acid tert-butyl ester 9a

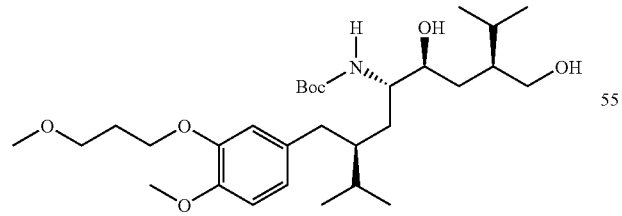

(9a)

a) A solution of 1 g of the pyrrolidine 8 in 17 mL of THF is cooled to −78° C. and 17 mL of ammonia condensed into the flask. To the mixture is added 0.44 g of Sodium and the resulting dark-coloured mixture stirred over night at −78° C. To the mixture is added 2.6 g of ammonium chloride. The mixture is allowed to warm to r.t. (ammonia evaporates off and unreacted sodium is dissolved) before addition of 40 mL of toluene and 1.9 g of acetic acid. After 10 min 25 mL of water is added and the phases are separated. The aqueous phase is back-extracted with 25 mL of toluene, then the combined organic phases are washed four times with 1:1 water-brine before drying over sodium sulfate and evaporating in vacuum. Purification of the crude oily product (0.86 g) on silica gel, eluting with ethyl acetate-heptane affords e.g. 0.71 g of pure 9a. $^1$H-NMR ($CDCl_3$, 300K): 6.8 (2H), 6.7 (1H), 4.7 (1H), 4.1 (2H), 3.8 (3H), 3.5-3.7 (5H), 3.4-3.5 (1H), 3.4 (3H), 2.7-2.8 (1H), 2.4-2.5 (3H), 2.0-2.2 (2H), 1.5-1.8 (8H), 1.4 (9H), 0.8-0.9 (12H).

b) A solution of 1.0 g of the pyrrolidine 8 in 2.5 mL of tetrahydrofuran is added to a mixture of 0.37 g of sodium in 5 mL of ammonia and 2.5 mL of tetrahydrofuran at −50° C. The mixture is stirred for 3 h then 2.56 g of ammonium chloride is added and the mixture allowed to warm to r.t. To the mixture is then added 40 mL of toluene, 1.9 g of acetic acid and 25 mL of water. The phases are separated and the aqueous phase is back-extracted with 25 mL of toluene. The combined organic phases are then washed with 4×120 mL of 1:1 water-brine, dried over sodium sulfate and the solvent removed in vacuum, affording e.g. 0.76 g of the product 9a as an oil.

VII. Synthesis of (2R,3S,5S)-5-((2S,4S)-5-Hydroxy-4-isopropyl-tetrahydro-furan-2-yl)-3-isopropyl-2-[4-methoxy-3-(3-methoxypropoxy)-phenyl]-pyrrolidine-1-carboxylic acid tert-butyl ester 10

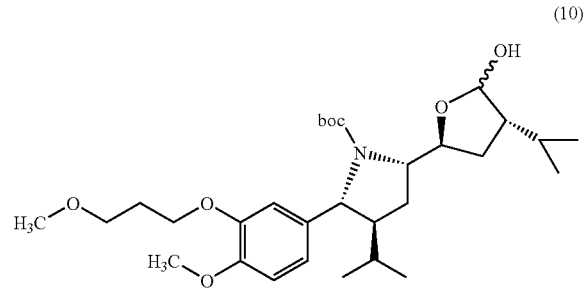

(10)

Variant employing SO$_3$/pyridine: A solution of 0.20 g of alcohol 9 in 5 mL of methylene chloride is treated with 3 mL of dimethyl sulphoxide and 0.2 g of triethylamine at 0° C. A solution of 0.24 g of the SO$_3$/pyridine complex in 4 mL of dimethyl sulphoxide is added dropwise within 15 minutes at 0° C. The reaction is stirred for 40 minutes at 0° C. then warmed to room temperature and stirred for a further 2 hours.

Water (10 mL) and heptane (15 mL) are added, and the resulting mixture is extracted. The organic phase is washed with 15 mL of a 10% aqueous solution of sodium hydrogen sulphate followed by water (15 mL) and 10% aqueous sodium bicarbonate solution. The organic phase is removed in vacuum to give e.g. 0.18 g of the lactol 10 M$^+$+=536.

VIII. Synthesis of (2R,3S,5S)-3-isopropyl-5-((2S, 4S)-4-isopropyl-5-oxo-tetrahydro-furan-2-yl)-3-isopropyl-2-[4-methoxy-3-(3-methoxypropoxy)-phenyl]-pyrrolidine-1-carboxylic acid tert-butyl ester 11

A solution of 0.16 g of alcohol 9 in 3 mL of methylene chloride is treated with 0.005 g of TEMPO followed by portionwise addition of 0.20 g of (diacetoxyiodo)benzene. The mixture is stirred for 5 hours at room temperature after which time only lactol 10 can be detected. A further 0.20 g of diacetoxyiodo benzene is added and the reaction stirred for a further 24 hours at room temperature. Aqueous sodium thiosulphate solution (5 mL of 10%) and water (5 mL) are added and the phases are separated. The organic phase is washed with 10 mL of water and the solvent is removed in vacuum to give an oil. Chromatography on silica-gel gives e.g. 0.12 g of 11. [α]$_D$=+28.3° (1%, CHCl$_3$), mp.: 70-71.5° C., $^1$H-NMR (CDCl$_3$, 300K): 6.6-6.8 (3H), 4.3-4.4 (2H), 4.0-4.1 (2H), 3.7-3.8 (4H), 3.5-3.6 (2H), 3.3 (3H), 2.5-2.6 (2H), 2.3-2.4 (1H), 2.0-2.2 (5H), 1.4-1.7 (4H), 1.4 (9H), 1.0 (3H), 0.9 (3H), 0.8 (6H).

Alternatively, 76 mg of lactol 10 are dissolved in 2 ml of acetonitrile and 80 mg of molecular sieve is added. To the suspension is added a solution of 21 mg of N-methylmorpholine N-oxide and 2.5 mg of TPAP (tetra-N-propylammonium perruthenate) in 1 ml of acetonitrile. After 2 hours stirring at room temperature the reaction is complete. The solvent is evaporated in vacuum and the residue is dissolved in ethyl acetate and filtered via a short pad if silicagel. The filtrate is evaporated in vacuum to give 77 mg of compound 11.

Alternatively, to a solution of 0.68 g of the alcohol 9a in 18 mL of acetonitrile, containing 0.7 g of 4 Å powdered molecular sieves, is added 0.59 g of N-methylmorpholine-N-oxide and 44 mg of tetrapropylammonium perruthenate, and the mixture is stirred overnight. After removal of the solvent in vacuum, the residue is taken up in ethyl acetate, filtered through silica gel, washing with ethyl acetate, and the solvent again removed in vacuum. Purification of the crude oily product (0.72 g) on silica gel, eluting with ethyl acetate-heptane affords e.g. 0.57 g of the pure Lactone 11.

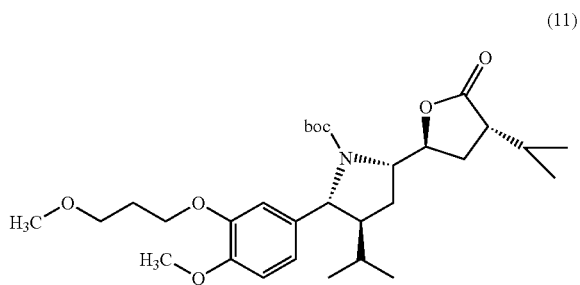

(11)

IX. Synthesis of (2R,3S,5S)-5-[(1S,3S)-3-(2-carbamoyl-2-methyl-propylcarbamoyl)-1-hydroxy-4-methyl-pentyl]-3-isopropyl-2-[4-methoxy-3-(3-methoxy-propoxy)-phenyl]-pyrrolidine-1-carboxylic acid tert-butyl ester 12:

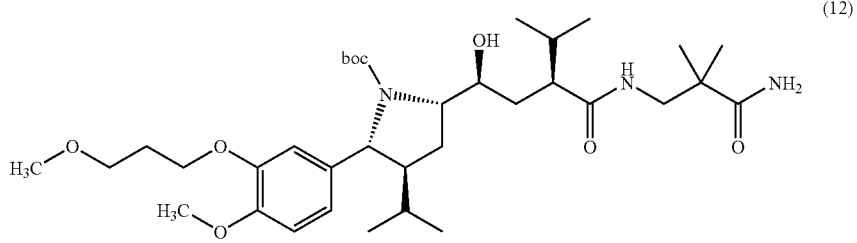

(12)

A solution of 0.08 g of lactone 11, 0.052 g of 3-amino-2,2-dimethylpropionamide and 0.014 g of 2-hydroxypyridine in 0.3 mL of tert-butylmethyl ether containing 0.02 g of triethylamine is stirred for 18 hours at 83° C. The reaction mixture is then cooled to room temperature and diluted with 2 mL of toluene and washed with 2 mL of 10% aqueous sodium hydrogen sulphate solution. The organic phase is separated and washed with water, and the solvent is removed in vacuum to give an oil. This oil is suspended in 5 mL of hexane and stirred. The solid is removed by filtration and the hexane removed in vacuum to give e.g. 0.06 g of amide 12 as a foam. $M^+$–H=648.

X. Synthesis of ((1S,2S,4S)-4-(2-carbamoyl-2-methyl-propycarbamoyl)-2-hydroxy-1-{(S)-2-[4-methoxy-3-(3-methoxy-propoxy)-benzyl]-3-methylbutyl}-5-methyl-hexyl)-carbamic acid tert-butyl ester 13:

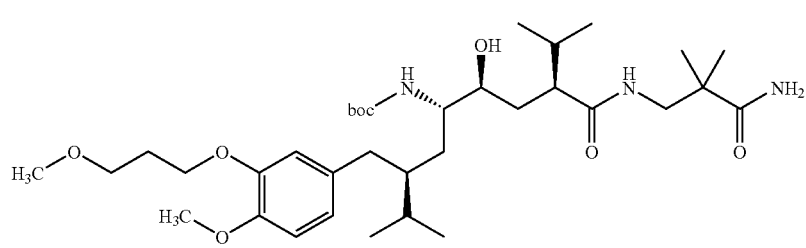

(13)

A solution of 0.037 g of amide 12 is dissolved in 1 mL of tetrahydrofurane and cooled to −78° C. Liquid ammonia is added followed by 0.0042 g of lithium metal. The deep blue solution is stirred for 2 hours at −78° C., and then 0.35 g of ethanol is added and the mixture is stirred for 30 minutes at −78° C. Ammonium chloride (0.15 g) is added and the mixture is warmed to room temperature. The organic phase is partitioned between water and ethyl acetate. The organic phase is separated and the solvent removed in vacuum. The residue is stirred with heptane and filtered. Removal of the heptane produces 13 identical with an authentic sample. $M^+$+H=652

XI. (2S,4S,5S,7S)-5-amino-N-(2-carbamoyl-2-methylpropyl)-4-hydroxy-2-isopropyl-7-[4-methoxy-3-(3-methoxypropoxy)benzyl]-8-methylnonanamide)

Product 13 is dissolved in a mixture of 4.0M hydrochloric acid in dioxane. The solution is stirred for 24 hours at room temperature and neutralized with solid sodium bicarbonate. The suspension is filtered and the solvent removed in vacuum to give the product as a foam (for characterization see e.g. EP 0 678 503, Example 137).

From the free compound or the hydrochloride salt obtainable, for example the hemifumarate salt of the title compound can be prepared, for example as described in U.S. Pat. No. 6,730,798, example J1 (comprising mixing with fumaric acid, dissolution in ethanol, filtration, evaporation of the obtained solution, re-dissolving of the residue in acetonitrile, inoculation with a small amount of the title compound's hemifumarate salt and isolation of the precipitating material), incorporated by reference herein especially with regard to this salt formation reaction.

The invention claimed is:

1. A process for the manufacture of a compound of the formula III,

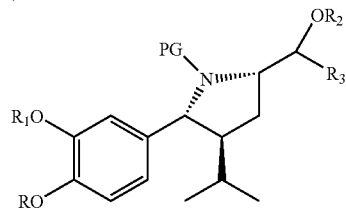

(III)

wherein
R is hydrogen, alkyl or alkoxyalkyl;
$R_1$ is hydrogen, alkyl or alkoxyalkyl;
$R_2$ is hydrogen or preferably a hydroxyl protecting group;
$R_3$ is hydrogen or unsubstituted or substituted alkyl; and
PG is an amino protecting group, especially one removable by hydrolysis, e.g. lower alkoxycarbonyl, such as tert-butoxycarbonyl or benzyloxycarbonyl;
or a salt thereof;
said process comprising reacting a compound of the formula I,

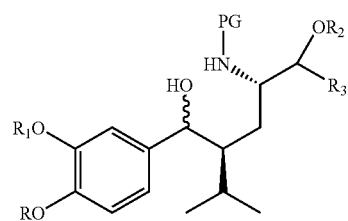

(I)

wherein R, $R_1$, $R_2$, $R_3$ and PG are as defined for a compound of the formula III, with a reagent able to transform hydroxy in formula I into X where X is a group other than hydroxy or hydrogen, especially a leaving group, especially a reagent selected from a hydrohalic acid, a thionyl halogenide, $PX^*_3$, $POX^*_3$, $PX^*_5$, $POX^*_5$ wherein X* is a halogennide, a combination of triphenylphosphine and halogen, and an active derivative of an organic sulfonic acid.

2. A process according to claim 1, where in the compounds of the formula III and the compounds of the formula I
$R_1$ is $C_1$-$C_7$-alkoxy-$C_1$-$C_7$alkyl, especially 3-methoxypropyl;
R is $C_1$-$C_7$-alkoxy, especially methoxy; and
$R_3$ is hydrogen, while the remaining moieties are as defined in claim 1.

* * * * *